United States Patent
Quackenbush et al.

(10) Patent No.: US 7,106,067 B2
(45) Date of Patent: Sep. 12, 2006

(54) CALIBRATION PLUG FOR INVASIVE AND NON-INVASIVE ELECTRODELESS CONDUCTIVITY SENSORS AND METHODS OF USING THE SAME CALIBRATION PLUG

(75) Inventors: John K. Quackenbush, Middleboro, MA (US); Stephen B. Talutis, Milton, MA (US)

(73) Assignee: Invensys Systems, Inc., Foxboro, MA (US)

( * ) Notice: Subject to any disclaimer, the term of this patent is extended or adjusted under 35 U.S.C. 154(b) by 0 days.

(21) Appl. No.: 11/064,157

(22) Filed: Feb. 23, 2005

(65) Prior Publication Data

US 2005/0200370 A1    Sep. 15, 2005

(51) Int. Cl.
*G01N 27/02* (2006.01)
*G01R 27/08* (2006.01)
*G01R 35/00* (2006.01)

(52) U.S. Cl. .................. 324/446; 324/601; 324/691
(58) Field of Classification Search ............... 324/446, 324/691, 601
See application file for complete search history.

(56) References Cited

U.S. PATENT DOCUMENTS

| | | | | |
|---|---|---|---|---|
| 4,825,168 A | | 4/1989 | Ogawa et al. ............ 324/439 |
| 5,341,102 A | * | 8/1994 | Akiyama et al. ......... 324/445 |
| 5,519,644 A | | 5/1996 | Benton .................... 702/88 |
| 5,793,214 A | * | 8/1998 | Wakamatsu ............... 324/601 |
| 5,959,455 A | | 9/1999 | Brown .................... 324/445 |
| 6,369,579 B1 | | 4/2002 | Riegel .................... 324/439 |
| 6,414,493 B1 | | 7/2002 | Rezvani ................... 324/442 |
| 6,538,246 B1 | | 3/2003 | Wada et al. ............ 250/214 SW |
| 6,720,773 B1 | | 4/2004 | Brown .................... 324/449 |
| 6,754,601 B1 | | 6/2004 | Eryurek et al. ........... 702/104 |
| 6,781,389 B1 | | 8/2004 | Colvin et al. ............ 324/789 |

FOREIGN PATENT DOCUMENTS

JP     2000131286 A    *    5/2000

* cited by examiner

*Primary Examiner*—Anjan Deb
*Assistant Examiner*—Amy He
(74) *Attorney, Agent, or Firm*—Sampson & Associates, P.C.

(57) ABSTRACT

A calibration plug provides resistance simulation for calibrating toroidal conductivity sensors. This calibration plug includes a resistive element of predetermined electrical resistance coupled in series between electrical leads which may be engaged with a circuit element to form an electrical circuit. The toroidal sensor includes one or more toroidal coils defining a central bore extending therethrough, a cell factor, and a full scale conductivity value. The predetermined resistance of the resistive element is determined in accordance with the following equation:

$$\text{Resistance in Ohms} = \frac{\text{[geometric] cell factor (of } EC \text{ sensor)} \times 1000}{\text{Full scale conductivity value in millisiemens/cm}}$$

and the calibration plug further includes indicia identifying one or more toroidal conductivity sensors for which the plug is configured.

15 Claims, 5 Drawing Sheets

FIG. 5

CALIBRATION PLUG FOR INVASIVE AND NON-INVASIVE ELECTRODELESS CONDUCTIVITY SENSORS AND METHODS OF USING THE SAME CALIBRATION PLUG

FIELD OF INVENTION

The present invention relates generally to calibration of invasive and non-invasive electrodeless conductivity (EC) sensors and more particularly to calibration plug used for this calibration.

BACKGROUND

The need to measure the conductivity of typically aqueous fluids is ubiquitous throughout various industries such as pharmaceuticals and chemicals, food, metals and mining, steam generation, hydrocarbon processing, textiles and the power sector. Determination of the conductivity of process fluids used in these and other such industries is accomplished by measuring the resistance of the binary or non-binary ionic solution exhibiting the property of conductivity.

One type of EC sensor is a toroidal inductive conductivity sensor. These sensors typically include two toroid transformer coils that are suitably spaced apart. One coil is called a drive coil or transmitter coil, and the other is called a receiver coil or sense coil or a detection coil. When the toroidal conductivity sensor is immersed in a conductive fluid (or the fluid is otherwise disposed within or passed through the toroids) and the drive coil is electrically excited or energized by an alternating current source, the drive coil generates a changing magnetic field.

The changing magnetic field induces a current loop in the sample fluid. The magnitude of the induced current is indicative of the conductivity of the fluid. The current in the fluid in turn induces a current in the receiver coil, which the analyzer measures. The current in the receiver coil is directly proportional to the conductivity of the fluid. This type of invasive toroidal sensor is typically used for conductivity values that exceed 1+ microsiemens/cm.

These EC sensors are also used in conjunction with an analyzer or transmitter that converts the resistance measurements provided by the sensor to actual conductivity values, typically as microsiemens/cm or millisiemens/cm also known as micromhos/cm or millimhos/cm respectively wherein 1 millimho/cm equals 1000 micromho/cm.

The accuracy of this measurement depends in large part on the initial calibration of the specific EC sensor with its associated electronic circuitry. This initial calibration identifies for the electronic circuitry, a low-end conductivity point (typically but not necessarily 'zero') and a high range (or full scale) conductivity point, these points corresponding to distinct conductivity values. These conductivity values are each inputted to the electronic circuitry in the form of an input signal corresponding to a specific resistance value. This specific resistance value is determined by the following equation:

$$\text{Resistance in ohms} = \frac{[\text{geometric}] \text{ cell factor (of } EC \text{ sensor}) \times 1000}{\text{Full scale conductivity value in millisiemens/cm}} \quad \text{(Equation 1)}$$

A typical current method for calibration is explained below.

A decade resistance box known to a person skilled in the art is used wherein the lead therefrom is passed through the bore of the toroid of the EC sensor, when a specific desired resistance of a particular value (equivalent of a desired conductivity value used in Equation 1) is to be input to the electronic circuit. This specific desired resistance value is then 'dialed in' on the decade resistance box and the calibration reading in the electronic circuit is read. Thus the calibration of the sensor for that desired conductivity value is completed.

A primary advantage of this method is that the decade resistance box typically permits the input of a specific desired resistance value by manually adjusting a series of graduated resistance levels on the dials of the resistance box, which adjustment is known to the person skilled in the art. Thus any resistance value that a decade box is capable of providing can be selected for calibration.

There are, however, disadvantages of this method using a decade resistance box. For example, if calibration of the sensor is to be completed away from the shop bench, which is a very common occurrence, then the decade resistance box must be transported to one or more locations, which may be problematic as decade resistance boxes are typically large and cumbersome to transport. In addition, human errors are possible in determining the specific desired resistance value. (For example, an error may occur in using the above mentioned equation or an error may be made in cell factor determination.) Even in the event the correct resistance value is determined, human errors may be introduced by inaccurate input of the desired resistance using the graduated dials of the decade resistance box. In addition, the decade resistance box itself may be 'out of tolerance' (for example, due to temperature effects). Moreover, decade resistance boxes typically do not provide precision resistance values, which may result in undesirable inaccuracies.

Alternatively, an EC sensor may be calibrated by use of a single resistor or a pair of resistors mechanically attached to a loop of wire that is passed through the toroidal bore of the sensor. An advantage of this method is that the resistors are lighter and smaller than the decade resistance box. This approach, however, also has disadvantages. For example, human errors are possible in determining the specific desired resistance value (such as in solving the above mentioned equation and/or in determining the particular cell factor). Also, poor quality connections between the resistance wire and the resistor(s) may degrade resistance values and generate inaccurate calibration results. Human errors are also possible in converting resistor color codes.

In view of the above, there is a need to develop a method and apparatus for calibrating an EC sensor, which addresses the above mentioned disadvantages.

SUMMARY

An aspect of the invention includes a calibration plug for providing resistance simulation for calibrating a toroidal conductivity sensor. The calibration plug includes a resistive element having a predetermined electrical resistance and a loop cable having a proximal end and a distal end. The proximal end is electrically coupled to one side of the resistive element, while the distal end is removably coupled to another side of the resistive element. The toroidal sensor includes toroidal coils defining a central bore extending therethrough, and has a predetermined cell factor and full scale conductivity value. The loop cable may be formed into one or more loops extending through the bore with the proximal and distal ends coupled to the resistive element to provide a predetermined calibration resistance. This resistance value is determined in accordance with the following equation:

$$R \text{ (in Ohms)} = \frac{[\text{geometric}] \text{ cell factor (of } EC \text{ sensor}) \times 1000 \times (N[\text{number of loops}])^2}{\text{Full scale [or 1-loop, if } N > 1]\text{ conductivity value in millisiemens/cm}}$$

where N is the number of loops; the "full scale conductivity value" is the conductivity value of one loop; and the calibration plug further includes indicia identifying one or more toroidal conductivity sensors for which the plug is configured.

Another aspect of the invention includes a calibration plug for providing resistance simulation for calibration of a toroidal conductivity sensor. This calibration plug includes a resistive element having a predetermined electrical resistance. The resistive element is coupled in series between electrical leads which may be engaged with a circuit element to form an electrical circuit. The toroidal sensor includes one or more toroidal coils defining a central bore extending therethrough, a cell factor, and a full scale conductivity value. The resistive element has a predetermined electrical resistance value determined in accordance with the following equation:

$$\text{Resistance in ohms} = \frac{[\text{geometric}] \text{ cell factor (of } EC \text{ sensor}) \times 1000}{\text{Full scale conductivity value in millisiemens/cm}}$$

and the calibration plug further includes indicia identifying one or more toroidal conductivity sensors for which the plug is configured.

A still further aspect includes a method of calibrating a toroidal conductivity sensor using a calibration plug of one of the preceding aspects of the invention. The method includes placing an analyzer, coupled to the conductivity sensor, in calibration mode and forming one or more loops by passing a loop cable a predetermined number of times through the central bore of the sensor, and having the ends of said loop cable connected to said calibration plug. Output of the analyzer is then recorded and correlated to the number of the loops as respective calibration values.

BRIEF DESCRIPTION OF FIGURES

A more complete understanding of the invention and a fuller appreciation of the many attendant advantages thereof will be derived by reference to the following detailed description when considered in connection with the accompanying drawings wherein.

LIST OF PARTS

10, 10' - - - calibration plug
12 - - - resistive element
14 - - - loop cable
15 - - - receptacle
15' - - - second receptacle
16 - - - toroidal conductivity sensor
16' - - - non-invasive toroidal conductivity sensor
17 - - - probe
17' - - - second probe
18 - - - central bore space
20 - - - single loop
22 - - - two loops
24 - - - three loops
26 - - - analyzer
28 - - - calibration port
30 - - - process conduit

DETAILED DESCRIPTION

Figure 1:
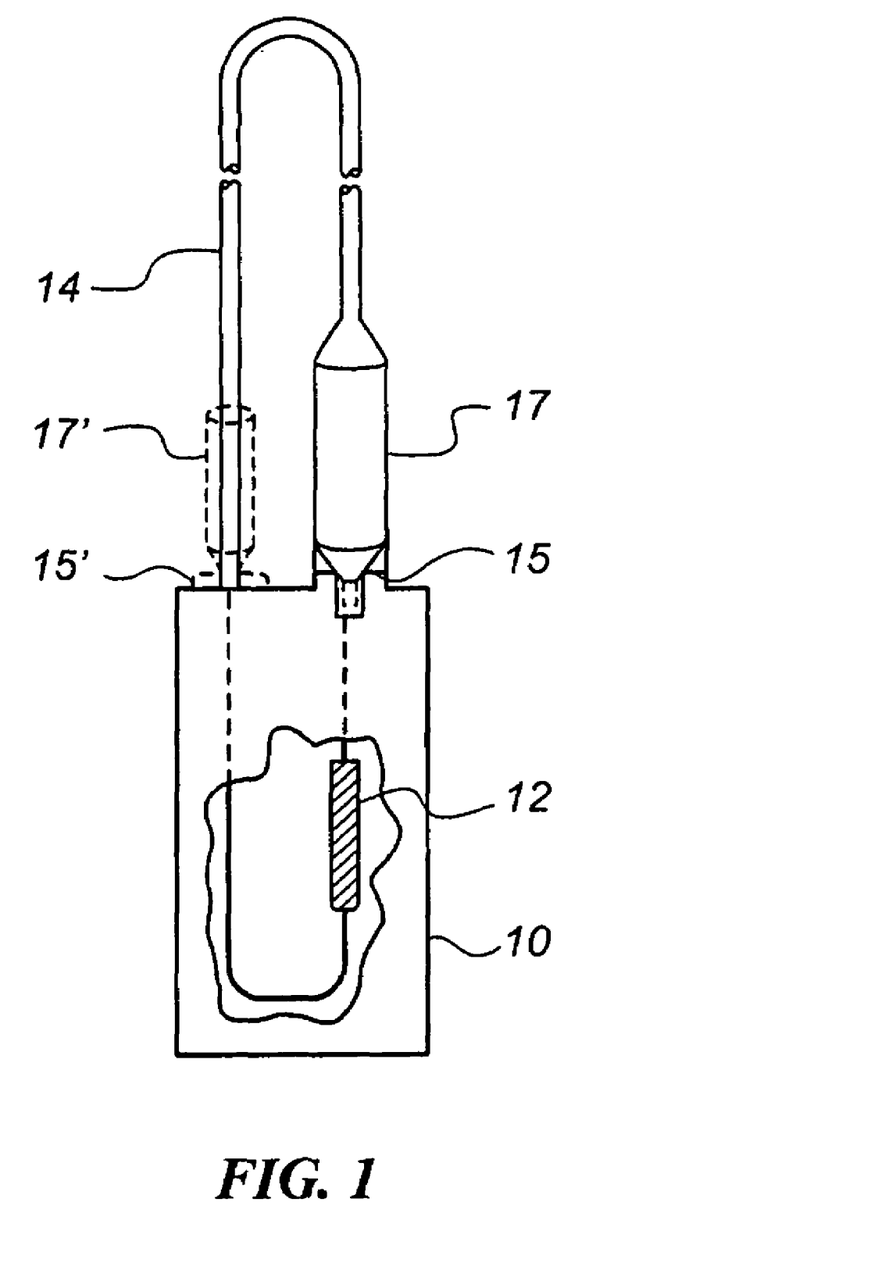
FIG. 1 is a schematic elevational view, with portions broken away for clarity, and optional portions shown in phantom, of an embodiment of the present invention including a calibration plug with resistive element.

Referring to FIG. 1, an embodiment of the invention is shown as calibration plug 10, which may be used in lieu of the conventional decade resistance box known to those skilled in the art. The calibration plug 10 has a resistive element or elements 12 which is electrically coupled in series with a cable 14 and a receptacle 15. In the embodiment shown, a proximal end of cable 14 is coupled (e.g., hardwired) to a lead extending from one side of element 12. A distal end of the cable includes a probe 17 sized and shaped for removable receipt within a receptacle 15 coupled to the other side of element 12 to form a complete electrical circuit. Calibration plug 10 thus provides a small, lightweight, easily transportable, relatively simple, precision resistance of a specific, predetermined resistance value that is nominally unaffected by temperature and which does not have any loose connections. These aspects substantially ensure that the predetermined resistance will not degrade and lead to associated inaccuracies.

In this embodiment, for convenience, the proximal end of cable 14 is shown as hardwired to plug 10. However, the skilled artisan should recognize that cable may be removably connected to the plug with any suitable connector(s), such as with a second receptacle and probe arrangement such as shown in phantom at 15' and 17', without departing from the spirit and scope of the present invention. Similarly, although representative connectors have been schematically shown at 15, 17, 15', 17', the skilled artisan should recognize that nominally any type of electrical connection means, including but not limited to any various well-known connectors such as those known as Banana, BNC, RCA, Coaxial, RJ-XX, etc., may be used without departing from the spirit and scope of the present invention.

In particular embodiments, the calibration plug is manufactured/customized for a specific, predetermined EC sensor model (for example, a model having a particular geometric cell factor) and for a specific conductivity value (for example, full-scale). The calibration plug may be manufactured using conventional fabrication techniques. The appropriate resistance value R for resistive element 12 may be determined using Equation 2 below, using 1 for the value of N:

$$R \text{ (in Ohms)} = \frac{1000 \times N^2 \text{[where } N = \text{number of loops]}}{\frac{\text{[geometric] cell factor (of EC sensor)} \times}{\text{Full scale [or 1 − loop, if } N > 1]}} \quad \text{(Equation 2)}$$
$$\text{conductivity value in millisiemens/cm}$$

where N is the number of loops and the full scale conductivity value is the conductivity value of one loop.

Figure 2:
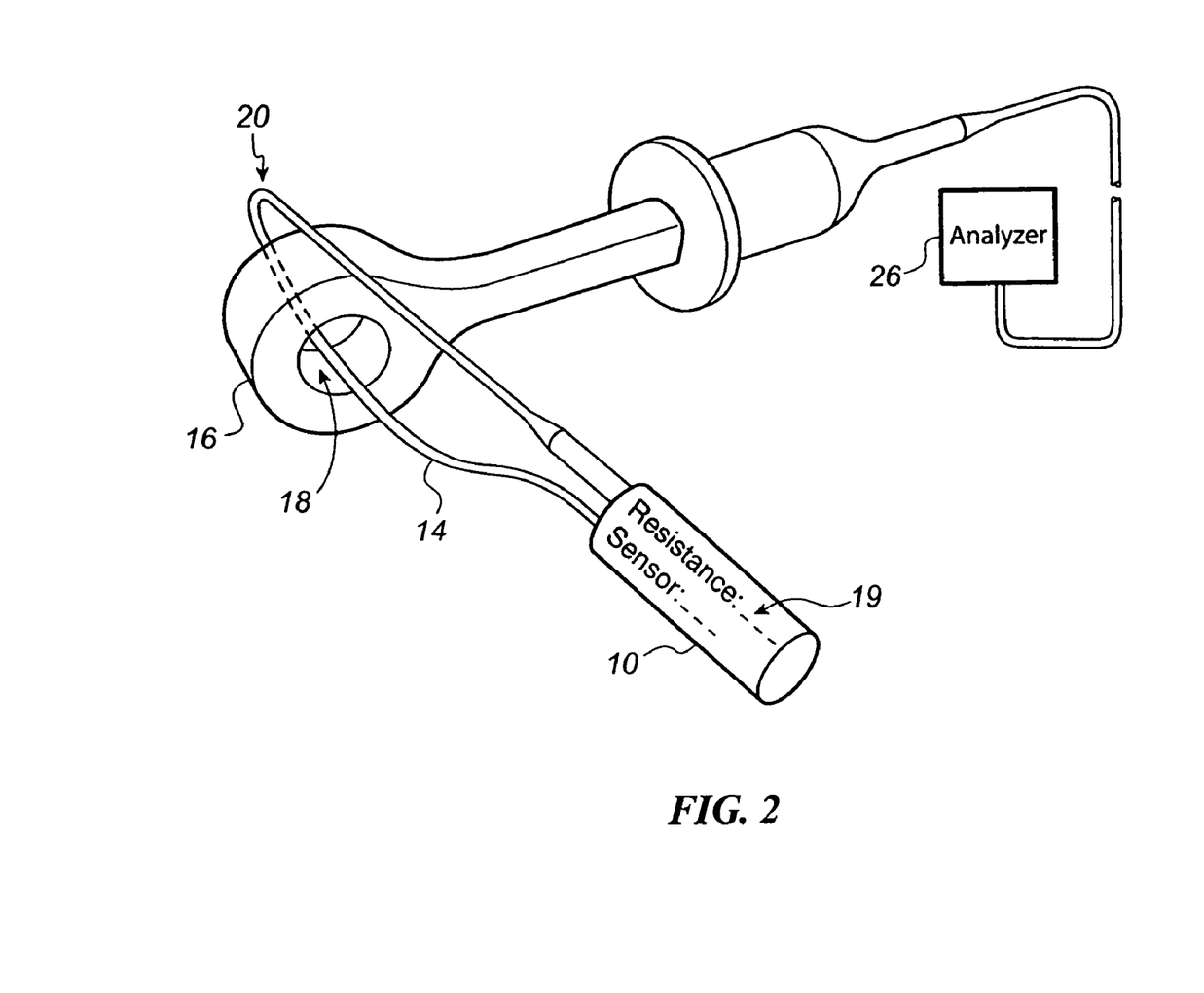
FIG. 2 is a schematic perspective view of the embodiment of FIG. 1 in a representative application including a single-loop formation of the calibration plug in use with a toroidal conductivity sensor.

Referring to FIG. 2, probe 17 of calibration plug 10 may be passed once through the bore 18 of a conventional toroidal sensor 16 before being connected to receptacle 15, so that cable 14 forms a single loop 20 through sensor 16 as shown. This single loop arrangement provides a single, predetermined resistivity (and conductivity) value for use in calibrating the toroidal sensor 16, e.g., using conventional calibration routines associated with the sensor's analyzer 26.

As also shown, plug 10 (and plug 10' described hereinbelow) may be provided with indicia 19 corresponding to the resistance value of the plug (e.g., in Ohms), its full scale conductivity value, and/or the particular EC sensor(s) for which the resistance of plug 10 has been configured. Indicia 19 may also include the resistance/conductivity values associated with multiple loops of lead wire 14 as discussed in greater detail hereinbelow.

Figure 3:
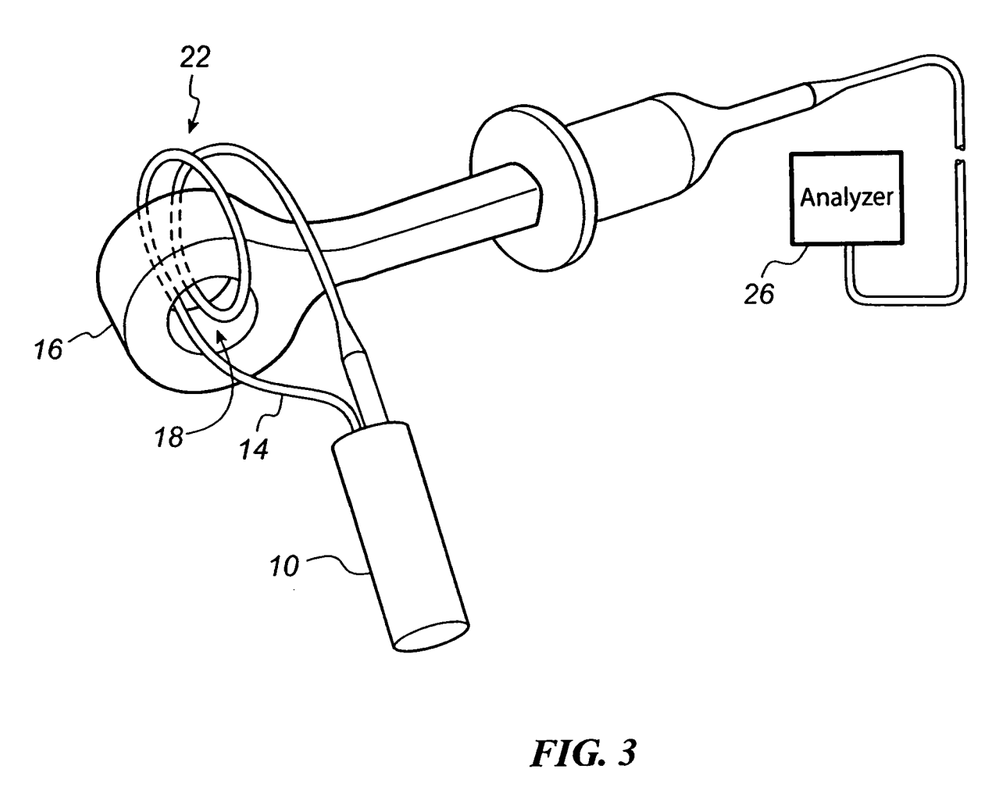
FIG. 3 is a view similar to that of FIG. 2, in a representative application including a two-loop formation of the calibration plug in use with a toroidal conductivity sensor.

Referring to FIG. 3, when probe 17 and cable 14 are passed through the bore 18 two times to form two loops 22, the same calibration plug 10 provides toroidal sensor 16 with another specific conductivity value for calibration thereof. In the embodiments shown, the resistance value provided by the two-loops 22 is calculated using Equation 2, where N=2 (N being the number of loops formed by cable 14 through the bore 18), and the conductivity value used in the denominator of the equation is the inverse of the resistance value (i.e., 1/R) calculated above for the single loop embodiment, in millisiemens. The resulting resistance value seen by sensor 16 in this embodiment is thus higher (and the conductivity lower) than that that seen by the sensor in the single loop 20 arrangement of FIG. 2.

Figure 4:
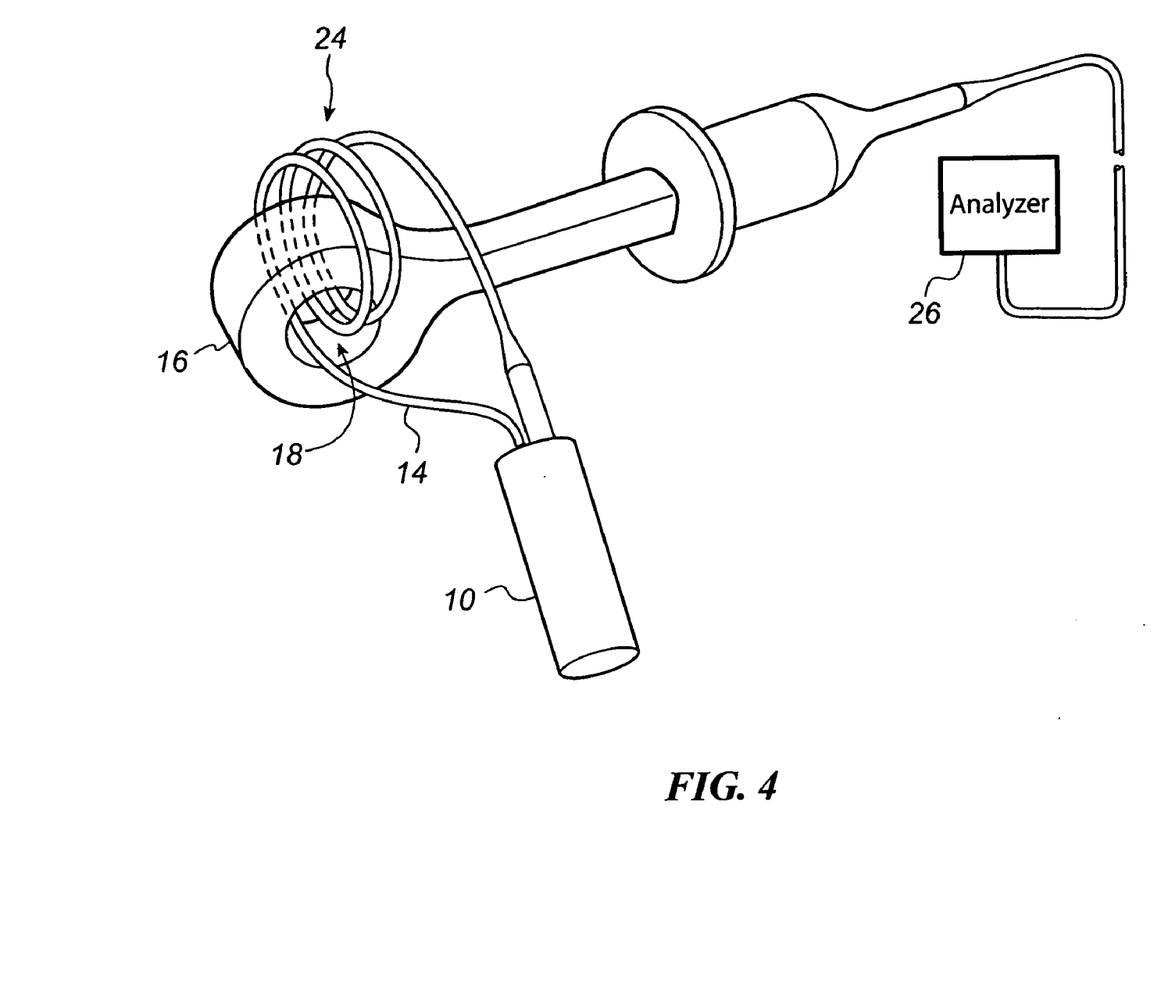
FIG. 4 is a view similar to that of FIGS. 2 and 3, in a representative application including a three-loop formation of the calibration plug in use with a toroidal conductivity sensor.

Similarly, referring to FIG. 4, when probe 17 and cable 14 are passed through bore 18 three times to form three loops 24, the same calibration plug 10 provides toroidal sensor 16 with yet another specific resistance/conductivity value for calibration of the sensor. In this embodiment, the resistance value provided by these three loops 24 is calculated in the same manner as for the two loop calculation, while using N=3. The resulting resistance value seen by sensor 16 is yet higher (and the conductivity yet lower) than that provided by the two loops 22 of FIG. 3.

The conductivity value provided by single loop 20 may advantageously be used by analyzer 26 for full scale calibration of sensor 16. The values of conductivity provided by the two-loops 22 and/or three-loops 24 may be useful for checking linearity of output, and/or for checking alarm values.

In addition, although one, two, and three loops have been shown, those skilled in the art should recognize, in light of the instant disclosure, that calibration plug 10 may be configured to form more than three loops, e.g., with each additional loop providing sensor 16 with a distinct, progressively higher resistance value and lower equivalent conductance value.

Figure 5:
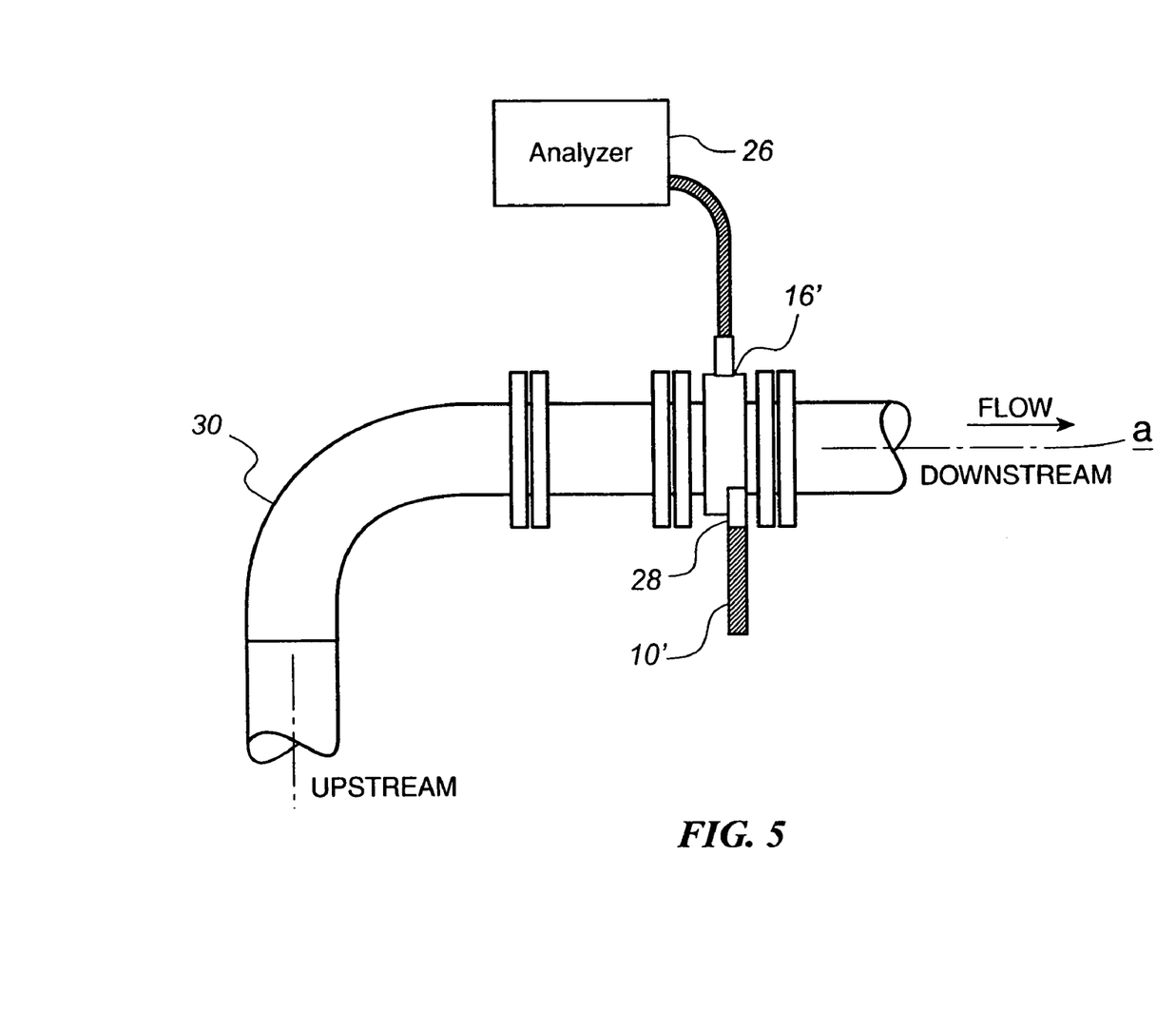
FIG. 5 is a plan view of an embodiment of the present invention installed in another representative application.

Turning now to FIG. 5, an alternate embodiment of the present invention includes calibration plug 10' which is substantially similar to plug 10, but without cable 14 and probe 17. Rather, the leads on either side of resistive element 12 are exposed, such as in the form of connector portions (e.g., receptacles) 15, 15' configured for coupling to a calibration port 28 of a conventional non-invasive toroidal conductivity sensor 16' as shown. An example of such a non-invasive sensor is an 871FT™ sensor available from Invensys Systems, Inc. (Foxboro, Mass.).

Sensor 16', including plug 10', is shown in a typical installation, within a fluid process conduit 30. The skilled artisan will recognize that the toroids of non-invasive toroidal conductivity sensor 16' effectively circumscribe conduit 30, so that the process fluid flows through the toroids without disruption, e.g., in a downstream direction indicated by arrow a as shown.

Once plug 10' is connected to calibration port 28 as shown, sensor 16' may be calibrated in an otherwise conventional manner, i.e., through use of analyzer 26. In this embodiment, plug 10' will generally be used to provide a single resistance/conductivity value, such as to provide a full scale calibration. However, one or more plugs 10' may alternatively be provided with lower conductance/higher resistance values, such as to provide sub-full scale calibration. In this regard, multiple plugs 10' of various conductance/resistance values may be used to test for linearity, alarms, etc.

Calibration plug 10' thus provides a small, lightweight, easily transportable, relatively simple, precision resistance of a specific, predetermined resistance value that is nominally unaffected by temperature and which does not have any loose connections. These aspects help ensure that the predetermined resistance will not degrade and lead to associated inaccuracies. The use of precision resistors in plugs 10 and 10' advantageously reduces or eliminates any adverse temperature effects.

Having described various embodiments of the present invention, exemplary methods of use thereof will now be described with reference to Tables I & II.

TABLE I

40 Providing calibration plug 10
42 Placing analyzer 26 into calibration mode
44 Forming at least one loop through the central bore of the sensor, with ends connected to plug 10
46 Optionally forming addition loops through the central bore
48 Recording analyzer output corresponding to number of the loops as respective calibration values.

Referring to Table I, an exemplary method includes providing 40 a calibration plug 10, placing 42 an analyzer 26 in calibration mode, and forming 44 one loop of loop cable by passing the cable through central bore of and around a toroidal conductivity sensor, thereby subjecting the sensor to a specific resistance value. Optionally, additional loops may be formed 46, such as to subject the sensor to other specific resistance values. Output of the analyzer corresponding to the number of loops may then be recorded 48.

TABLE II

50 Providing calibration plug 10'
52 Placing analyzer in calibration mode
54 Placing the calibration plug in the calibration port of the sensor
56 Communicably connecting said sensor and analyzer to one another
58 Recording analyzer output corresponding to the conductivity value of the calibration plug Referring to Table II, another exemplary method includes providing 50 a calibration plug 10', placing 52 an analyzer in calibration mode. The calibration plug 10' is then placed 54 into the calibration port 28 (FIG. 5) of the sensor 16', so that the calibration port and associated circuitry form the circuit element engaged by the calibration plug. In this manner, the calibration plug subjects the sensor to a specific resistance value. The analyzer is connected 56 to the sensor 16', and the output of the analyzer corresponding to the resistance of the plug 10' is recorded 58.

While the above description contains many specificities, these should not be construed as limitations in the scope of the invention, but rather as an exemplification of particular embodiments thereof. Accordingly, the scope of the invention should be determined not by the embodiments illustrated, but by the appended claims and their equivalents.

What is claimed is:

1. A calibration plug for providing resistance simulation for calibration of a toroidal conductivity sensor comprising:
   a resistive element having a predetermined non-adjustable electrical resistance;
   a loop cable having a proximal end and a distal end;
   said proximal end being electrically coupled to one side of said resistive element;
   said distal end being removably coupled to another side of said resistive element;
   wherein said resistive element is electrically couplable in series between said proximal end and said distal end of said cable;
   the toroidal sensor including one or more toroidal coils defining a central bore extending therethrough, a cell factor, and a full scale conductivity value;
   said loop cable being configured for forming one or more loops extending through the bore with the proximal and distal ends electrically coupled to said resistive element to provide a predetermined calibration resistance;
   the predetermined electrical resistance value of the resistive element being determined in accordance with the following equation:

$$R \text{ (in Ohms)} = \frac{[\text{geometric}] \text{ cell factor (of } EC \text{ sensor}) \times 1000 \times (N[\text{number of loops}])^2}{\text{Full scale [or 1-loop, if } N > 1] \text{ conductivity value in millisiemens/cm}}$$

wherein N is the number of said loops;
   wherein said full scale conductivity value is the conductivity value of one loop;
   the calibration plug further including indicia identifying one or more toroidal conductivity sensors for which the plug is configured; and
   wherein the calibration plug is a discrete unitary device.

2. A method of calibrating a toroidal conductivity sensor comprising:
   a) providing the calibration plug of claim 1;
   b) placing an analyzer, coupled to the conductivity sensor, in calibration mode;
   c) forming one or more loops by passing a loop cable a predetermined number of times through the central bore of the sensor, and having the ends of said loop cable connected to said calibration plug; and
   d) recording analyzer output corresponding to number of the loops as respective calibration values.

3. A calibration plug for providing resistance simulation for calibration of a toroidal conductivity sensor comprising:
   a resistive element having a predetermined non-adjustable electrical resistance;
   a plurality of electrical leads coupled to said resistive element;
   said resistive element being electrically coupled in series between said electrical leads;
   said electrical leads configured for operable engagement with a circuit element to form an electrical circuit including said resistive element;
   the toroidal sensor including one or more toroidal coils defining a central bore extending therethrough, a cell factor, and a full scale conductivity value;
   the resistive element having a predetermined electrical resistance value R1 determined in accordance with Equation 1:

$$R_1 \text{ (in Ohms)} = \frac{[\text{geometric}] \text{ cell factor (of } EC \text{ sensor}) \times 1000}{\text{Full scale conductivity value in millisiemens/cm}} \quad \text{(Equation 1)}$$

the calibration plug further including indicia identifying one or more toroidal conductivity sensors for which the plug is configured; and
   wherein the calibration plug is a discrete unitary device.

4. The calibration plug of claim 3, comprising the toroidal conductivity sensor.

5. The calibration plug of claim 3, wherein said electrical leads comprise connector means for removably coupling to the circuit element.

6. The calibration plug of claim 5, wherein said connector means comprise one or more connector portions sized and shaped for engaging complementary sized and shaped portions of the circuit element.

7. The calibration plug of claim 6, wherein said circuit element comprises a loop cable having a proximal end coupled to a lead depending from one side of said resistive element, and a probe disposed at a distal end of said cable, said probe sized and shaped for receipt within a receptacle to form a complete electrical circuit including said resistive element.

8. The calibration plug of claim 3, wherein said circuit element is selected from the group consisting of a loop cable and a calibration port of the toroidal sensor.

9. The calibration plug of claim 8, comprising the loop cable configured for forming one or more loops extending through the bore with the proximal and distal ends electrically coupled to said resistive element to provide a predetermined calibration resistance, the predetermined calibration resistance $R_2$ determined in accordance with Equation 2:

$$R_2 \text{ (in Ohms)} = \frac{[\text{geometric}] \text{ cell factor (of } EC \text{ sensor}) \times 1000 \times (N[\text{number of loops}])^2}{1/R_1 \text{ (from Equation 1) in millisiemens/cm.}} \quad \text{(Equation 2)}$$

wherein N is the number of loops.

10. The calibration plug of claim 9, further comprising indicia identifying resistance values associated with the number of loops.

11. The calibration plug of claim 9 wherein said loop cable forms one loop.

12. The calibration plug of claim 9 wherein said loop cable forms two loops.

13. The calibration plug of claim 9 wherein said loop cable forms three loops.

14. A method of calibrating a non-invasive toroidal conductivity sensor comprising:
   a) providing the calibration plug of claim 3;
   b) placing an analyzer in calibration mode;
   c) disposing the calibration plug in the calibration port of the sensor, wherein the calibration port comprises the circuit element;
   d) communicably connecting said sensor and analyzer to one another; and
   e) recording analyzer output corresponding to the conductivity value of the calibration plug.

15. A calibration plug for providing resistance simulation for calibration of a toroidal conductivity sensor comprising:
   resistive means for providing a predetermined non-adjustable electrical resistance;
   electrical lead means for coupling to said resistive element;
   said resistive means being electrically coupled in series between said electrical lead means;
   said electrical lead means configured for operable engagement with a circuit element to form an electrical circuit including said resistive element;
   the toroidal sensor including one or more toroidal coils defining a central bore extending therethrough, a cell factor, and a full scale conductivity value;
   said resistive means having a predetermined electrical resistance value determined in accordance with Equation 1:

$$\text{Resistance in Ohms} = \frac{\text{[geometric] cell factor (of } EC \text{ sensor)} \times 1000}{\text{Full scale conductivity value in millisiemens/cm}} \quad \text{(Equation 1)}$$

the calibration plug further including indicia means for identifying one or more toroidal conductivity sensors for which the plug is configured; and
   wherein the calibration plug is a discrete unitary device.

* * * * *